(12) United States Patent
Bergström et al.

(10) Patent No.: US 6,254,387 B1
(45) Date of Patent: Jul. 3, 2001

(54) DENTAL IMPLANT COMPONENT

(75) Inventors: Nils Gustaf Bergström, Vagnhärad (SE); Hansruedi Carisch, La Chaux-de-Fonds (CH); Leif Broberg, Mölndal (SE); Anders Holmén, Hovås (CH)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 09/355,723

(22) PCT Filed: Jul. 21, 1999

(86) PCT No.: PCT/SE99/01299

§ 371 Date: Aug. 3, 1999

§ 102(e) Date: Aug. 3, 1999

(87) PCT Pub. No.: WO00/04841

PCT Pub. Date: Feb. 3, 2000

(30) Foreign Application Priority Data

Jul. 23, 1998 (SE) .................................................. 9802603

(51) Int. Cl.[7] .................................................. A61C 8/00
(52) U.S. Cl. ............................................. 433/49; 433/173
(58) Field of Search .................................. 433/49, 50, 173, 433/174, 201.1, 202.1

(56) References Cited

U.S. PATENT DOCUMENTS

| | | |
|---|---|---|
| 2,042,200 | 5/1936 | Torp . |
| 5,064,373 | 11/1991 | Staubli et al. . |
| 5,362,237 | 11/1994 | Chalifoux . |
| 5,468,150 | 11/1995 | Brammann . |
| 5,538,426 | 7/1996 | Harding et al. . |
| 5,733,123 * | 3/1998 | Blackloke et al. .................... 433/173 |
| 5,788,494 * | 8/1998 | Phimmasone ........................ 433/213 |
| 5,873,722 * | 2/1999 | Lazzara et al. ...................... 433/173 |

\* cited by examiner

*Primary Examiner*—Ralph A. Lewis
(74) *Attorney, Agent, or Firm*—White & Case LLP (57) ABSTRACT

A set of dental implant components for use in fabricating a dental prosthesis (25) comprising a support component (19) for inclusion in a model of a jaw having a support end (17) and a socket (21); a sleeve cylinder (15) on which the dental prosthesis or a core part of the dental prosthesis is to be fabricated, the sleeve cylinder having a distal end adapted to engage with the support end of the support component, a proximal end and a channel extending from a distal opening in the distal end to a proximal opening in the proximal end; and an access passage-forming post (1) having a distal section (9) which presents a distal end (11) of the post and a proximal section (7) which presents a proximal end (3) of the post, the post being adapted to be disposed in an operational position when the distal end of the sleeve cylinder engages with the support end of the support component in which the distal section (9) of the post is releasably secured in the socket in the support component through the proximal opening of the channel in the sleeve cylinder and in which the proximal section (7) of the post protrudes from the proximal opening of the channel in the sleeve cylinder. The distal section of the access-passage forming post is releasably securable in the socket in the support component by a biasing force which biases the distal section and an inner surface of the socket together.

7 Claims, 4 Drawing Sheets

DENTAL IMPLANT COMPONENT

FIELD OF THE INVENTION

The present invention relates to a dental implant component, specifically an access passage-forming post for use in forming an access passage in a dental prosthesis or core part of a dental prosthesis.

BACKGROUND OF THE INVENTION

A dental prosthesis is one of the components which make up a dental implant which is a structure which is anchored to the jaw bone (maxilla or mandible) of a patient to replace one or more lost natural teeth. A dental implant comprises a dental prosthesis support structure which is anchored to the jaw bone of a totally or partially edentulous patient to support the dental prosthesis. The dental prosthesis support structure is typically formed by (i) one or more anchoring members (fixtures) implanted in the bone tissue of the maxilla or mandible, the number of fixtures used depending on whether the dental implant is to be for a single-tooth replacement, in which case a single fixture is used, or for replacement of a number of lost teeth, in which case one or, more usually, a plurality of fixtures will be used, and (ii) a transmucosal member (abutment) for each fixture, each abutment being connected to the coronal end of the associated fixture to bridge the soft tissue layer (gingiva) overlying the fixture site. A structure which presents one or more artificial replacement teeth—the dental prosthesis—is then connected to the coronal end(s) of the abutment(s), e.g. a crown for a single-tooth replacement or a bridge for replacement of a number of lost natural teeth.

To ensure that the dental prosthesis fits in with the prevailing conditions in the oral cavity, for instance the natural teeth still left in the maxilla or mandible, the dental prosthesis is fabricated with reference to a full-scale model of the toothless jaw prepared in a manner known per se. Usually incorporated in the model are one or more analogue components, the number corresponding to the number of fixtures implanted in the jaw bone. The or each analogue component has an end which is an analogue of the coronal end(s) presented by the dental prosthesis support structure, e.g. by the abutment(s). The or each analogue component is incorporated into the model so that the analogue end accurately reproduces the position and orientation that the associated coronal end of the dental prosthesis support structure has, or will have, in the jaw.

There is then provided for each analogue component a dental implant component which is commonly referred to in the art as a "cylinder" even though this component does not necessarily have a circular cross-section of constant diameter. Each such cylinder has a distal or apical end which complements the coronal end(s) of the dental prosthesis support structure and thus is able to seat on the analogue end of the associated analogue component. The cylinder(s) is seated on the analogue component(s) and then used in the fabrication of a dental prosthesis which fits in with the prevailing conditions in the oral cavity whereupon the dental prosthesis is transferred to the dental prosthesis support structure for anchorage to the jaw bone.

The manner in which the cylinder(s) is used in the fabrication of a dental prosthesis depends on whether the dental prosthesis is for a single-tooth replacement or for replacing a number of teeth and also on whether the prosthesis is to be a permanent prosthesis or a temporary prosthesis for use in the interim period while a permanent prosthesis is fabricated.

Permanent dental prostheses are typically formed by applying a wax pattern on the cylinder(s) and forming a cast structure on the cylinder(s) having the same profile as the wax pattern by the lost-wax casting process in which the cylinder-wax pattern assembly is surrounded by investment material and the wax pattern then removed by heating to leave a mould for a precious or semi-precious metal such as gold to be poured into via a sprue passing through the investment material. In this regard, the cylinder(s) can be totally or partially formed of a burnout material, e.g. of a plastic such as polystyrene, in which case the burnout material is also selectively replaced by the precious or semi-precious metal. The use of the investment material, however, ensures that surface features provided at the apical end(s) of the cylinder(s), for example the faces of a polygon, which enable the cylinder(s) to index with the coronal end(s) of the dental prosthesis support structure are retained in the cast structure when presented by burnout material.

For a permanent single-tooth dental prosthesis a porcelain layer will typically be fired onto the inner cast framework which includes, or is based on, a single cylinder to give a natural tooth appearance to the prosthesis. The wax pattern may or may not be shaped to give a tooth-like inner cast framework onto which the porcelain layer is fired. If the wax pattern is not shaped to a tooth-like form, the porcelain layer is built-up so as to give the prosthesis a tooth-like form.

Where a number of natural teeth are to be permanently replaced the dental prosthesis will typically comprise an inner cast framework which includes, or is based on, a number of cylinders and a range of artificial teeth (denture) mounted on the inner cast framework. In this instance, the wax pattern will typically splint the cylinders on the analogues in the model to form a cast framework which can bridge across the spaced-apart coronal ends of the dental prosthesis support structure and the denture will be mounted on the casting either before or after the casting is mounted on the dental prosthesis support structure. Alternately, the dental prosthesis may be formed by applying an isolated wax pattern to each cylinder to form individual castings which are then mounted to the coronal ends of the dental prosthesis support structure with the denture then being mounted onto the castings.

For an overview on the formation of permanent dental prostheses see inter alia *'Dental Implants: A Guide for the General Practitioner'*, Michael Norton, Quintessence Publishing, 1995, Chapters 4 and 5.

The use of temporary dental prostheses is well-known and the circumstances in which a temporary dental prosthesis is needed are documented in U.S. Pat. No. 5,259,759 (Jorneus et al/Nobelpharma AB). In the case of a temporary single-tooth dental prosthesis, the usual procedure is to form an acrylic resin artificial tooth on the cylinder by applying the acrylic resin to the outer surface of the cylinder when mounted on the analogue end of the analogue in the model, shaping the acrylic resin into a natural tooth form and then curing the acrylic resin.

The convention in the art is for a cylinder to be in the form of a sleeve, that is to say, having a distal or apical end for engagement with the analogue end of an analogue, and therefore the associated coronal end of the dental prosthesis support structure, a proximal or coronal end spaced from the apical end and an open-ended channel which extends from an opening in the apical end to an opening in the coronal end. Such cylinders are disclosed in U.S. Pat. No. 5,259,759 supra, U.S. Pat. No. 5,527,183 (O'Brien/Collaborative Enterprises, Inc.), U.S. Pat. No. 5,533,898 (Mena), U.S. Pat.

No. 5,439,380 (Marlin), U.S. Pat. No. 5,180,303 (Hornberg et al/Regents of the University of California) and U.S. Pat. No. 5,234,339 (Grigereit/Kulzer, Inc.). In some of these U.S. patents the cylinders are fixed directly to a fixture, that is to say, the need for an abutment in the dental prosthesis support structure is obviated.

By using a sleeve cylinder in the formation of a dental prosthesis for the replacement of a plurality of lost teeth, e.g. a bridge, an inner cast framework having open-ended channels therethrough can be formed. In the case of a double construction bridge (see Chapter 5, 'Dental Implants: A Guide for the General Practitioner' supra) these channels act as access passages for screws to pass through and secure the inner cast framework to the dental prosthesis support structure. The denture is then cemented to the inner cast framework screw-retained to the dental prosthesis support structure. In a regular bridge, the access passages can communicate with access passages formed in the denture when the denture is cemented to the inner cast framework. The cemented assembly can then be screw-retained to the dental prosthesis support structure via the communicating access passages.

In the case of a single-tooth dental prosthesis, e.g. a crown, the use of a sleeve cylinder allows the dental prosthesis to be cemented extra-orally to a coronal member of the dental prosthesis support structure such as an abutment with the cemented assembly then being added to the apical structure of the dental prosthesis support structure already anchored to the maxilla or mandible, as will be discussed more fully hereinafter.

In the case of permanent dental prostheses the formation of the access passages is as a result of a post being inserted into each sleeve cylinder when mounted on the associated analogue in the model to an operational position in which (i) the post is releasably secured to the analogue with the trailing end of the post projecting from the opening in the coronal end of the sleeve cylinder to a height greater than that to which the wax pattern is to be built, and (ii) the post forms a close fit with the opening in the coronal end of the sleeve cylinder. The wax pattern is then built-up around the post whereby removal of the post after the wax pattern has been completed leaves a passage in the wax pattern which communicates with the channel in the sleeve cylinder. The passage so formed in the wax pattern is then reproduced in the casting.

The close fit of the post with the opening in the coronal end of the sleeve cylinder acts to prevent wax leaking into the sleeve cylinder prior to casting which might otherwise make it difficult for the prosthesis or core part thereof to be properly secured on the dental prosthesis support structure.

A post is also used in similar fashion when a sleeve cylinder is used for forming a temporary dental prosthesis. For example, to form a temporary single-tooth dental prosthesis the apical end of the sleeve cylinder is engaged to the analogue end of the analogue structure in the model of the partially edentulous patient and the post is inserted into the sleeve cylinder to an operational position in which (i) the post is releasably secured to the analogue structure with the trailing end of the post projecting from the opening in the coronal end of the sleeve cylinder to a height greater than that to which the acrylic tooth is to be built, and (ii) the post forms a close fit with the opening in the coronal end of the sleeve cylinder. Acrylic resin is then applied to the outer surface of the sleeve cylinder around the post, shaped into the form of a natural tooth which inter alia fits in with the surrounding dentition in the model and then cured.

The close fit of the post with the opening in the coronal end of the sleeve cylinder in this instance acts to prevent the acrylic resin leaking into the sleeve cylinder prior to curing which might otherwise make it difficult for the prosthesis to be properly secured on the dental prosthesis support structure. The post further acts to form a channel in the cured acrylic tooth which communicates with the channel in the sleeve cylinder or, in other words, to form an open-ended channel through the temporary single-tooth dental prosthesis through which, for example, a screw can pass to screw-retain the prosthesis to the dental prosthesis support structure.

To illustrate the fact that the use of a sleeve cylinder enables extra-oral connection of a single-tooth dental prosthesis to a coronal member of a dental prosthesis support structure, as mentioned briefly hereinabove, one can consider the case of securing a temporary single-tooth dental prosthesis of the type described to a dental prosthesis support structure having a coronal member which is a conventional abutment comprising (i) an abutment sleeve having an open-ended axial channel which sits on the coronal end of a fixture in which there is an internally-threaded socket, and (ii) an abutment screw which is inserted through the channel in the abutment sleeve to be screwed into the internally-threaded socket in the coronal end of the fixture to secure the abutment sleeve to the fixture through a head of the abutment screw bearing down on a shoulder in the channel of the abutment sleeve. The sleeve cylinder sub-structure of the temporary single-tooth dental prosthesis will be cemented to the sleeve of this two-part abutment. In this connection, the open-ended channel formed in the temporary single-tooth dental prosthesis by the post enables the sleeve cylinder to be cemented to the abutment sleeve extra-orally and the assembly so formed to be placed on the coronal end of the fixture with the abutment screw then being inserted through the prosthesis-abutment sleeve assembly for screw engagement in the internally-threaded socket in the fixture. The channel in the prosthesis would then be filled in with a cosmetic material.

In the above illustration of extra-oral connection it is conceivable that the abutment sleeve could be releasably secured in the model in place of an analogue thereof, for example on an analogue of the fixture, whereby the sleeve cylinder is placed on the abutment sleeve during the fabrication of the dental prosthesis. In this case, the post could be secured in an internally threaded socket in the fixture analogue or, where the abutment screw is used to screw retain the abutment sleeve to the fixture analogue, in the abutment screw itself. More generally, there are other conceivable instances in which the coronal members of a dental prosthesis support structure may be incorporated in a model for use in combination with a sleeve cylinder during fabrication of a dental prosthesis prior to being anchored to the jaw bone.

Hitherto proposed access passage-forming posts have been releasably securable to the support component for the sleeve cylinder in the model by providing the posts with a screw threaded distal end for screw retention in an internally-threaded socket in the support component. An aim of the present invention is to provide a simpler connection between the access passage-forming post and the support component for the sleeve cylinder.

SUMMARY OF THE INVENTION

According to the present invention there is provided a set of dental implant components for use in fabricating a dental prosthesis comprising:

a support component for inclusion in a model of a jaw having a support end and a socket;

a sleeve cylinder on which the dental prosthesis or a core part of the dental prosthesis is to be fabricated, the sleeve cylinder having a distal end adapted to engage with the support end of the support component, a proximal end and a channel extending from a distal opening in the distal end to a proximal opening in the proximal end; and an access passage-forming post having a distal section which presents a distal end of the post and a proximal section which presents a proximal end of the post, the post being adapted to be disposed in an operational position when the distal end of the sleeve cylinder engages with the support end of the support component in which the distal section of the post is releasably secured in the socket in the support component through the proximal opening of the channel in the sleeve cylinder and in which the proximal section of the post protrudes from the proximal opening of the channel in the sleeve cylinder;

characterised in that the distal section of the access-passage forming post is releasably securable in the socket in the support component by a biasing force which biases the distal section and an inner surface of the socket together.

In an embodiment of the invention such as the one hereinafter to be described the socket in the support component and the distal section of the post are adapted such that the distal section is releasably securable in the socket through an interference fit.

In an embodiment of the invention such as the one hereinafter to be described the access-passage forming post is adapted to produce the biasing force and the biasing force so produced acts to bias the distal section of the access-passage forming post against the inner surface of the socket in the support component.

In an embodiment of the invention such as the one hereinafter to be described the distal section of the post is compressible inwardly against the biasing force and the socket in the support component and the distal section of the post are adapted such that the distal section is releasably securable in the socket by the biasing force biasing the distal section outwardly against the inner surface of the socket.

In an embodiment of the invention such as the one hereinafter to be described the distal section of the access-passage forming post is slotted to provide a plurality of resilient fingers.

In an embodiment of the invention such as the one hereinafter to be described the socket in the support component has an entrance which is shaped for compressing the distal section of the access-passage forming post inwardly. As an example, the entrance may taper inwardly in the distal direction as would be the case if the entrance was countersunk.

Preferably, the socket in the support component is unthreaded, as in the embodiment hereinafter to be described.

The support component may be formed from one or more elements. For instance, the support component may be an analogue element whose support end is an analogue of a coronal end of a fixture or abutment sleeve on which the distal end of the sleeve cylinder engages. In this case, the socket may be in the support end. Alternatively, the support component may comprise an analogue element having an end which is an analogue of a coronal end of a fixture and in which the socket is provided and an abutment sleeve mountable on the analogue end and having the support end for the distal end of the sleeve cylinder to engage with.

An exemplary embodiment of the invention will now be described with reference to the accompanying Figures of drawings.

DETAILED DESCRIPTION OF THE EXEMPLARY EMBODIMENT OF THE INVENTION

There will now follow a detailed description of a set of dental implant components according to an embodiment of the present invention with reference to their use in forming a single-tooth dental prosthesis.

Figure 1:
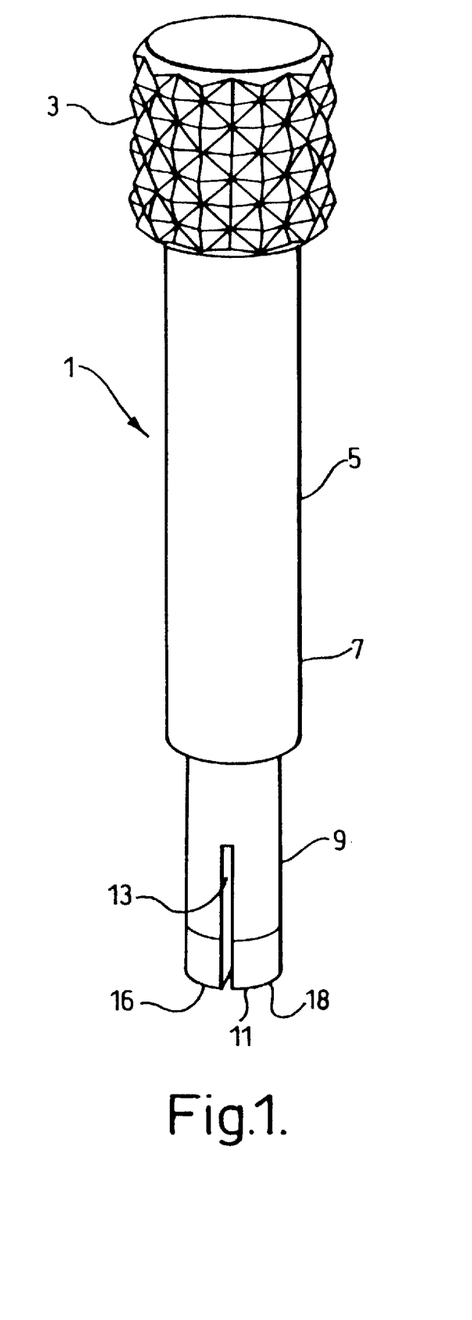
FIG. 1 is a perspective side view of an access passage-forming post of a set of dental implant components in accordance with the present invention.

In FIG. 1 there is shown an access passage-forming post 1 of the set formed from a metal such as steel or a plastic material. The post 1 has a generally circular cross-section and comprises a head 3 for handling of the post 1 and a cylindrical shaft 5 which depends from the head 3. The shaft 5 is stepped into a proximal section 7 of a first constant diameter and a distal section 9 of a second constant diameter less than the first constant diameter. The shaft 5 has a distal end 11 which is presented by the distal section 9 and in which an axially-extending radial slot 13 is provided to divide the distal end 11 into a pair of spaced apart resilient fingers 16, 18.

The fingers 16, 18 are compressible inwardly towards one another and release of the fingers 16, 18 when in a compressed condition results in a return force biasing the fingers 16, 18 outwardly away from one another to their respective rest positions shown in FIG. 1.

Figure 2:
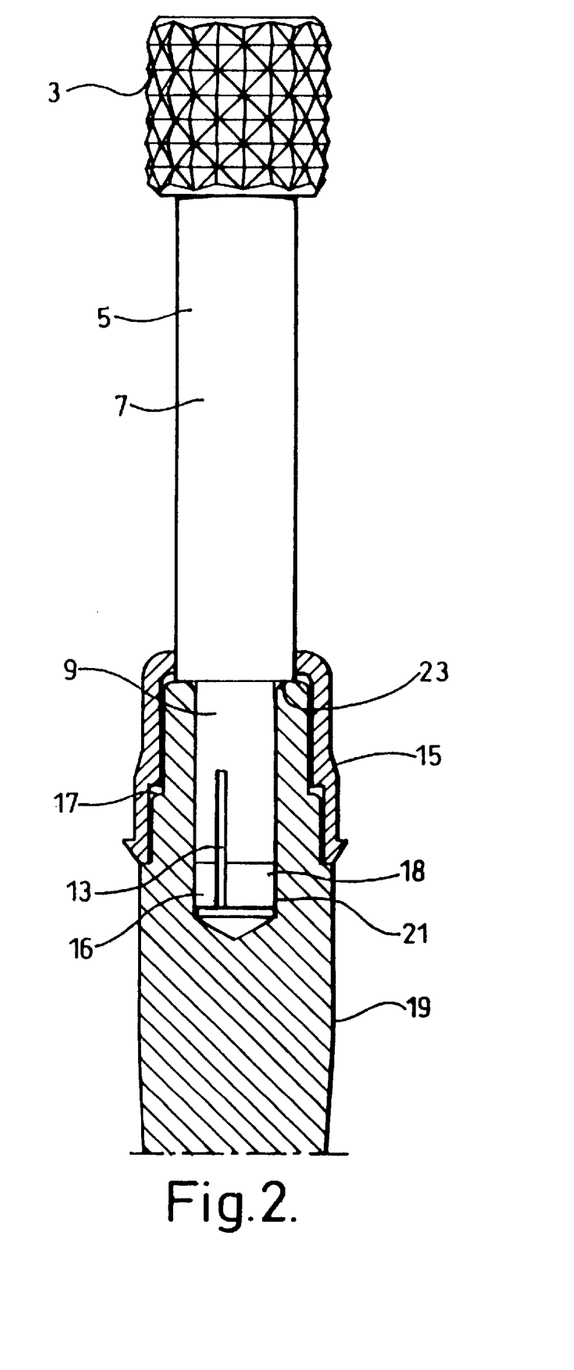
FIG. 2 is a partial cross-sectional view of the access-passage forming post inserted through a sleeve cylinder of the set into releasable securement with an abutment analogue of the set.

Referring to FIG. 2, there is shown a sleeve cylinder 15 of the set seated on an end 17 of an analogue structure 19 of the set which is contained in a model (not shown) of a toothless site in a jaw of a patient made by impression taking in a manner known per se. The sleeve cylinder 15 is of a generally circular cross-section and has an axially-extending, open-ended channel. The end 17 of the analogue structure 19 is an analogue of the coronal end of an abutment sleeve and is provided with an unthreaded blind bore 21 therein.

FIG. 2 shows the post 1 positioned in its operational position in which the distal section 9 of the shaft 5 projects into the channel of the sleeve cylinder 15 into the blind bore 21 in the analogue end 17 of the analogue structure 19 and the proximal section 7 of the shaft 5 abuts with the analogue end 17 of the analogue structure 19.

The first constant diameter of the proximal section 7 of the shaft 5 of the post 1 is selected such that in the operational position of the post 1 it plugs the channel of the sleeve cylinder 15. As well as plugging the channel of the sleeve cylinder 15 in the operational position of the post 1, the proximal section 7 of the shaft 5 is further sized to protrude from the sleeve cylinder 15 thereby spacing the head 3 of the post 1 from the sleeve cylinder 15.

The blind bore 21 in the analogue end 17 of the analogue structure 19 has a diameter which is marginally smaller than the second constant diameter of the uncompressed distal section 9 of the post 1 and has a countersunk entrance 23 thereto. It follows that as the distal section 9 of the shaft 5 of the post 1 is inserted into the blind bore 21 in the analogue end 17 of the analogue structure 19 during displacement of the post 1 towards the operational position the fingers 16, 18 of the post 1 are compressed inwardly against the biasing action of the return force. Accordingly, when the post 1 reaches the operational position the post 1 is releasably secured in the blind bore 21 in the analogue end 17 of the analogue structure 19 by an interference fit of the fingers 16, 18 in the blind bore 21 as a result of the return force biasing the fingers 16, 18 outwardly against the peripheral wall of the blind bore 21.

Figure 3:
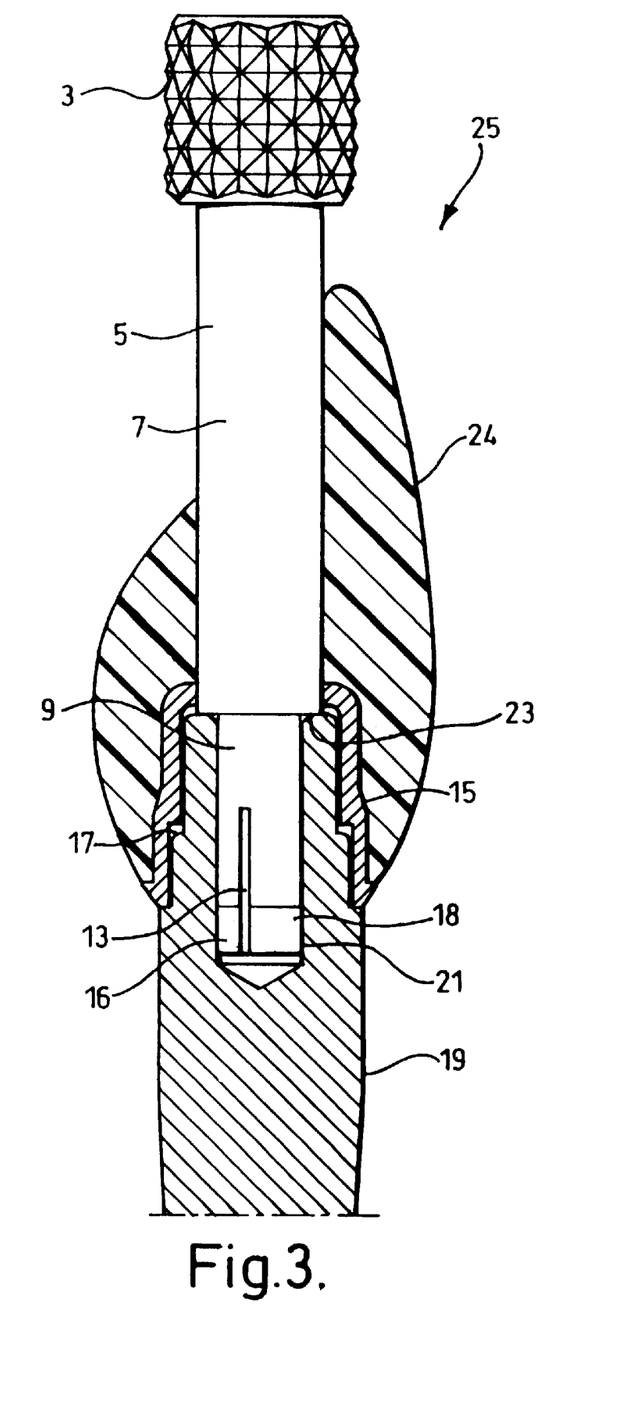
FIG. 3 is a partial cross-sectional side view corresponding to FIG. 2 with an acrylic resin artificial tooth fabricated on the sleeve cylinder around the post to form a single-tooth dental prosthesis with an access passage therethrough.

As shown in FIG. 3, after the post 1 has been mounted to the analogue structure 19 in the operational position thereof an artificial tooth 24 made of acrylic resin is formed on the sleeve cylinder 15 around the portion of the proximal section 7 of the shaft 5 of the post 1 protruding from the channel of the sleeve cylinder 15. This results in the formation of a single-tooth dental prosthesis 25 consisting of the acrylic resin artificial tooth 24 and the sleeve cylinder 15.

Figure 4:
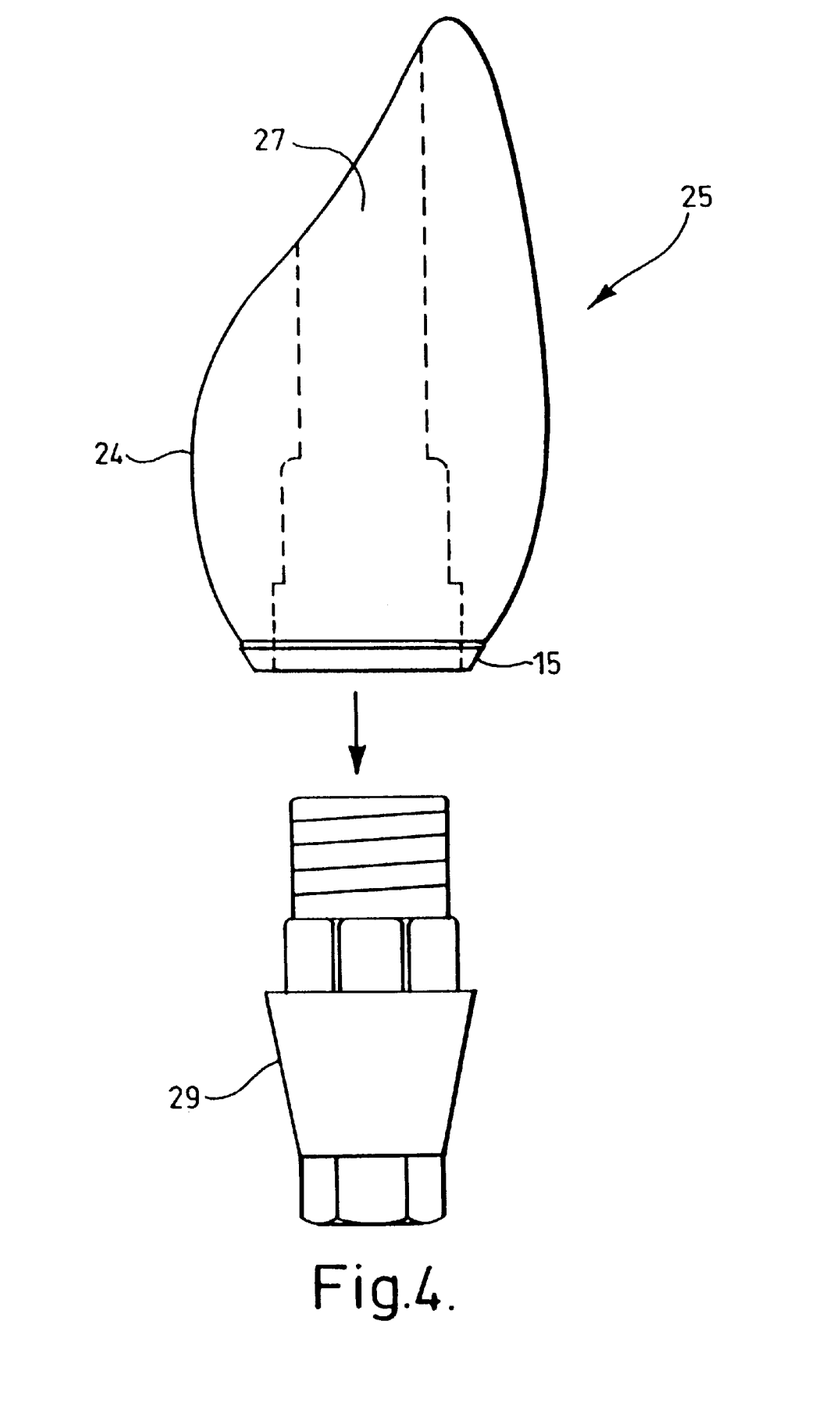
FIG. 4 is a schematic side view of the single-tooth dental prosthesis being cemented extra-orally to an abutment sleeve to form a prosthesis-abutment sleeve assembly.

As can be seen from FIG. 4, removing the post 1 from the blind bore 21 in the analogue end 17 of the analogue structure 19 by applying a pulling force to the post 1 sufficient to overcome the biasing action of the return force on the resilient fingers 16, 18 leaves a channel in the acrylic resin artificial tooth 24 which communicates with the channel in the sleeve cylinder 15 resulting in the single-tooth dental prosthesis 25 being provided with an axially-extending, open-ended channel 27.

Figure 5:
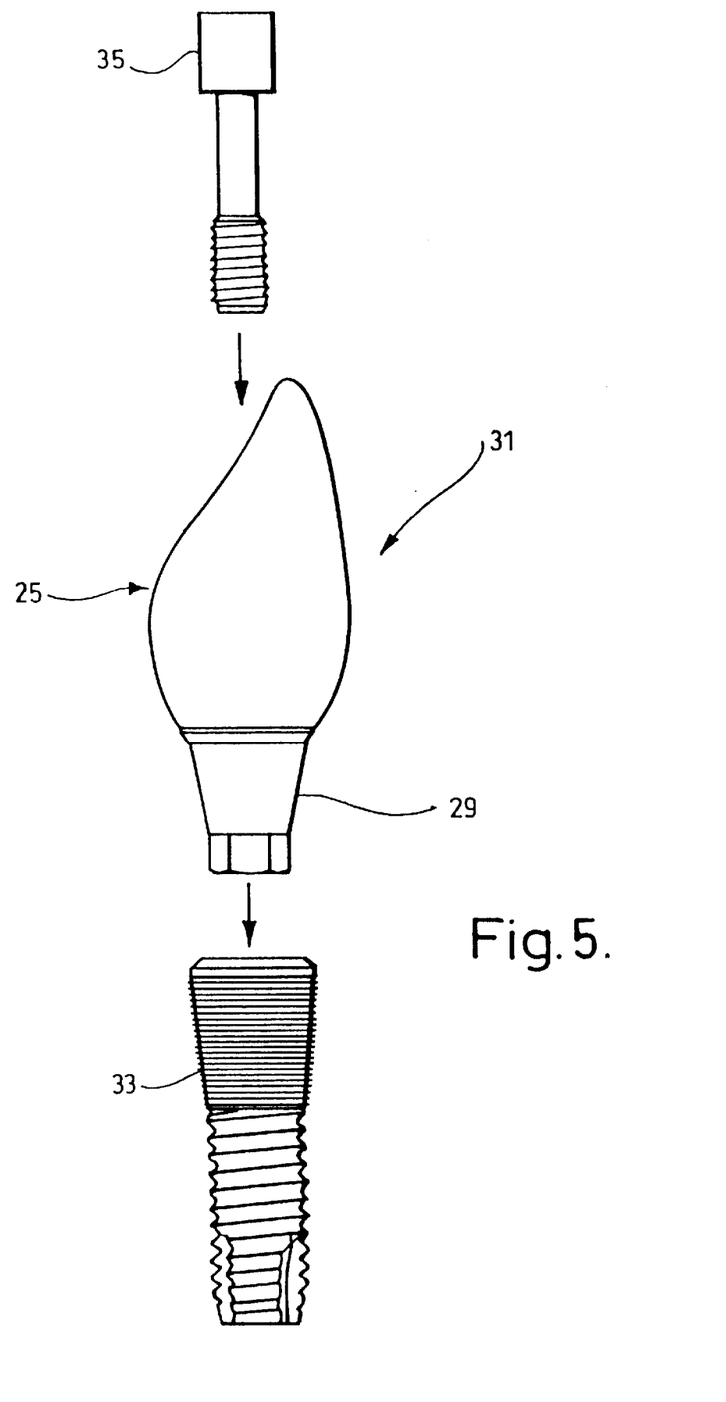
FIG. 5 is a side view of the prosthesis-abutment sleeve assembly being secured to a fixture by an abutment screw which can pass through an access passage in the assembly into an internally-threaded socket in the fixture.

The procedure for anchoring the single-tooth dental prosthesis 25 at the toothless site in the jaw of the patient will now be described with reference to FIGS. 4 and 5. Firstly, the single-tooth dental prosthesis 25 is cemented extra-orally to an abutment sleeve 29 which has a coronal end matching the analogue end 17 of the analogue structure 19 and an open-ended axial channel therethrough to form a prosthesis-abutment sleeve assembly 31. The prosthesis-abutment sleeve assembly 31 so formed has an axially-extending, open-ended channel therethrough (not shown) as a result of the axially-extending, open-ended channel 27 of the single-tooth dental prosthesis 25 communicating with the through channel of the abutment sleeve 29.

The prosthesis-abutment sleeve assembly 31 is then seated on a coronal end of a fixture 33 implanted in the maxilla or mandible of the patient at the toothless site and then screw retained to the fixture 33 by an abutment screw 35 which passes through the axially-extending, open-ended channel through the prosthesis-abutment sleeve assembly 31 into an internally-threaded socket (not shown) in the coronal end of the fixture 33.

Finally, the channel in the prosthesis-abutment sleeve assembly 31 is filled in with a cosmetic material.

The advantage of the first constant diameter of the proximal section 7 of the shaft 5 of the post 1 being such as to plug the channel in the sleeve cylinder 15 in the operational position of the post 1 will now be appreciated. The proximal section 7 of the shaft 5 forms a sealing fit in the sleeve cylinder 15 to prevent acrylic resin from leaking into the sleeve cylinder 15 during the preparation of the acrylic resin artificial tooth. If acrylic resin leaked into the sleeve cylinder 15 it could make it difficult for the sleeve cylinder 15 to seat properly on the abutment sleeve 29 in the formation of the prosthesis-abutment sleeve assembly 31 and also for the abutment screw 35 to be passed through the axially-extending, open-ended channel of the prosthesis-abutment sleeve assembly 31 into engagement with the internally threaded socket in the fixture 33.

As can be seen, the set of dental implant components described herein with reference to FIGS. 1 to 5 provides a simple mechanism for the access-passage forming post 1 to be releasably secured to the abutment analogue 19.

It will be appreciated that the present invention has been illustrated by an exemplary embodiment and can be varied in many ways within the scope defined by the appended claims. For instance, although the invention has been exemplified with reference to the fabrication of a single-tooth dental prosthesis with an acrylic resin artificial tooth the present invention has other applications, for example use in the fabrication of a cast inner framework of a single- or multi-tooth dental prosthesis. Moreover, individual features of the exemplary embodiment may have application in other embodiments of the invention either in isolation or in combination with other features from the exemplary embodiment.

Finally, the use of reference numerals from the accompanying Figures of drawings in the appended claims is for illustrative purposes and not to be construed as having a limiting effect on the scope of the claims.

What is claimed is:

1. A set of dental implant components for use in fabricating a dental prosthesis comprising:

a support component (19) for inclusion in a model of a jaw having a socket;

a sleeve cylinder on which the dental prosthesis or a core part of the dental prosthesis is to be fabricated, the sleeve cylinder being adapted to engage with the support component;

an access passage-forming post having a distal section and a proximal section, the post being adapted to be disposed in an operational position when the sleeve cylinder engages with the support component, wherein the access-passage forming post is releasable securable in the socket in the support component by a means for producing a biasing force which biases the post and an inner surface of the socket together when the post is secured in the socket.

2. A set of dental implant components according to claim 1, wherein, the socket in the support component and the distal section of the post are adapted such that the distal section is releasable securable in the socket through an interference fit.

3. A set of dental implant components according to claim 1 or 2, wherein the access-passage forming post is adapted to produce the biasing force and that the biasing force so produced acts to bias the distal section of the access-passage forming post against the inner surface of the socket in the support component.

4. A set of dental implant components according to claim 1, wherein a distal section of the post is compressible inwardly against the biasing force and that the socket in the support component and the distal section of the post are adapted such that the distal section is releasable securable in the socket by the biasing force biasing the distal section outwardly against the inner surface of the socket.

5. A set of dental implant components according to claim 4, wherein the distal section of the access-passage forming post is slotted (13) to provide a plurality of resilient fingers (16, 18).

6. A set of dental implant components according to claim 4 or 5, wherein the socket in the support component has an entrance (23) which is shaped for compressing the distal section of the access-passage forming post inwardly.

7. A set of dental implant components according to claim 1, wherein the socket is unthreaded.

* * * * *

UNITED STATES PATENT AND TRADEMARK OFFICE
CERTIFICATE OF CORRECTION

PATENT NO. : 6,254,387 B1
DATED : July 3, 2001
INVENTOR(S) : Bergström et al.

It is certified that error appears in the above-identified patent and that said Letters Patent is hereby corrected as shown below:

<u>Title page,</u>
Item [75], after "Hovås", delete "(CH)" and insert therefor -- (SE) --.

Signed and Sealed this

Fifteenth Day of January, 2002

Attest:

*Attesting Officer*

JAMES E. ROGAN
*Director of the United States Patent and Trademark Office*